United States Patent

Pauchon et al.

[11] Patent Number: 5,908,995
[45] Date of Patent: Jun. 1, 1999

[54] SYSTEM FOR MEASURING THE SOLUBILITY OF SOLID COMPOUNDS IN SUPERCRITICAL FLUIDS

[75] Inventors: Véronique Pauchon, Pertuis; Jacques Jose, Vilette de Vienne; Emmanuel Behar, Jouy le Moutier, all of France

[73] Assignee: Institut Francais du Petrole, Rueil-Malmaison, France

[21] Appl. No.: 08/886,038

[22] Filed: Jun. 27, 1997

[51] Int. Cl.⁶ .................................................. G01N 33/00
[52] U.S. Cl. ....................................................... 73/866
[58] Field of Search ............................................... 73/866

[56] References Cited

U.S. PATENT DOCUMENTS

| | | |
|---|---|---|
| 4,124,528 | 11/1978 | Modell . |
| 4,714,526 | 12/1987 | Pennisi et al. ............................ 230/49 |
| 5,169,687 | 12/1992 | Sunol . |
| 5,196,575 | 3/1993 | Sebastian ................................ 562/402 |
| 5,205,154 | 4/1993 | Lee et al. ................................ 73/23.35 |
| 5,217,590 | 6/1993 | Lauer et al. . |
| 5,266,205 | 11/1993 | Fulton et al. ............................ 210/639 |

FOREIGN PATENT DOCUMENTS

| | | |
|---|---|---|
| 0561114 | 9/1993 | European Pat. Off. . |
| 0692289 | 1/1996 | European Pat. Off. . |

*Primary Examiner*—Robert Raevis
*Attorney, Agent, or Firm*—Antonelli, Terry, Stout & Kraus, LLP

[57] ABSTRACT

A system for measuring the solubility of various solid organic compounds in supercritical fluids such as methane or carbon dioxide for example, and for studying the equilibrium between the solid phase and the supercritical phase in a wide pressure and temperature range is disclosed. The system comprises four functional units E1, E2, E3, E4. Unit E1 delivers a supercritical fluid (methane, $CO_2$, etc.), unit E2 comprises a sampling cell containing the compound to be solubilized, where the pressurized gas from unit E1 saturates on contact therewith, unit E3 is intended for sampling and bringing the sample into solution, and unit E4 is intended to receive the saturated fluid and to analyze it. The system allows dynamic solubilization to be performed with on-line or off-line analysis of the sample. The system can be applied for production of very pure compounds isolated from mixtures of heavy hydrocarbons for example or from alloys, or in the agribusiness for isolation of flavors.

21 Claims, 3 Drawing Sheets

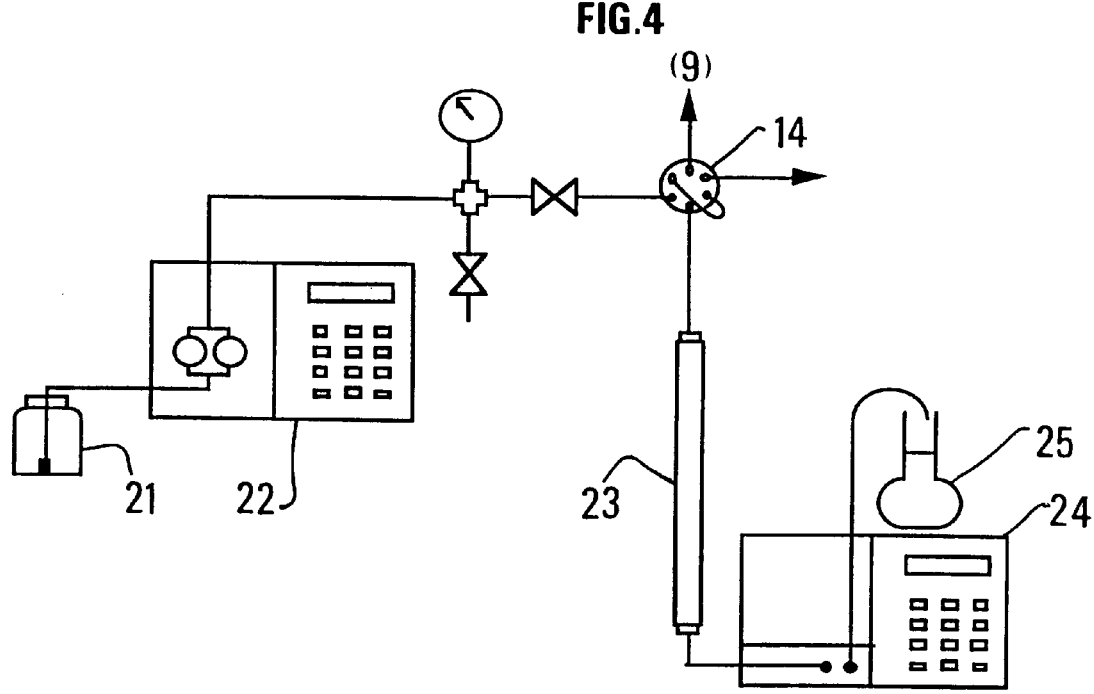
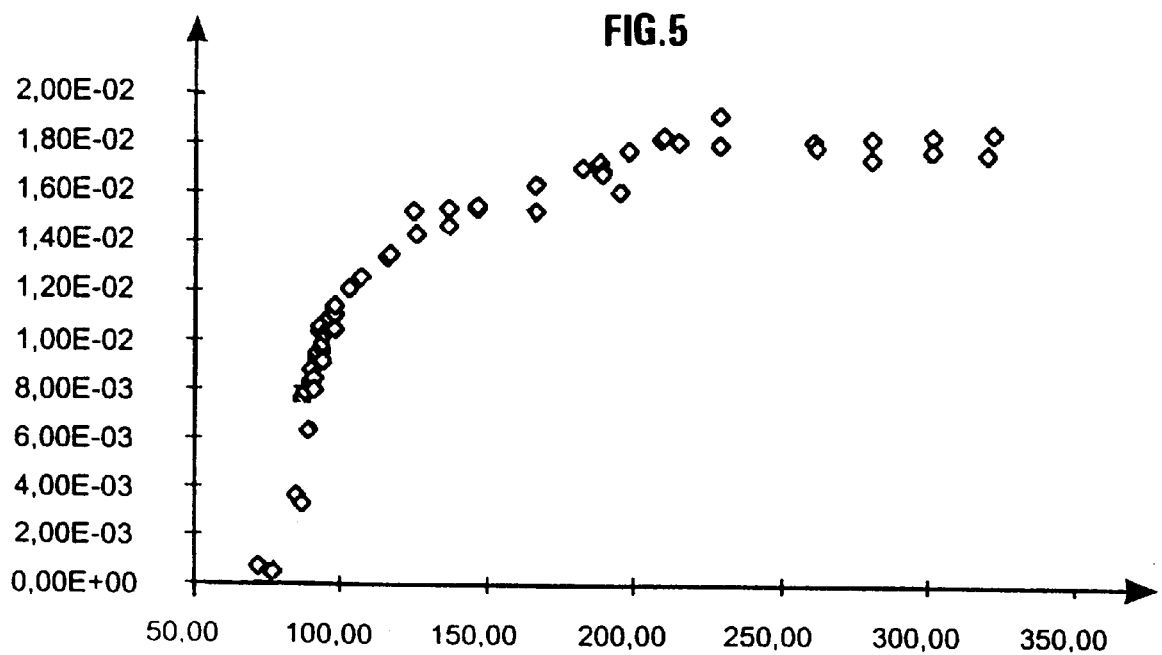

SYSTEM FOR MEASURING THE SOLUBILITY OF SOLID COMPOUNDS IN SUPERCRITICAL FLUIDS

BACKGROUND OF THE INVENTION

1. Field of the Invention

The present invention relates to a system for measuring the solubility of solid compounds in supercritical fluids such as methane or carbon dioxide.

The invention relates more particularly to the measurement of the solubility of various solid organic compounds in a supercritical gas ($CH_4$, $CO_2$, etc.) in a high pressure range ranging for example between 7 and 150 MPa, and at temperatures that may range between 20° and 200° C.

The system according to the invention allows dynamic solubilization and extraction with on-line or off-line analysis of the sample.

The system according to the invention has applications in many fields where constituents of mixtures are to be separated and more particularly when some of the constituents to be isolated occur in very small quantities, for example in the form of traces. The agrobusiness can for example be cited, where hop flavours used to produce beer are to be isolated, or caffein has to be separated to produce decaffeinated coffee. The invention also has applications in the aeronautical and space industry where very pure components isolated from mixtures or alloys are to be manufactured. Other applications exist in the petroleum, gas, chemical industries where solid heavy hydrocarbons are to be extracted from mixtures for example.

2. Description of the Prior Art

It should be noted that a gas is in the supercritical state when it is at a temperature and at a pressure that are higher than that of the critical point thereof, a fluid state that is neither liquid nor gaseous. The solvent power thereof in this state greatly depends on the temperature and the pressure.

The solubility of solids and of liquids in supercritical fluids can be determined by means of two different experimental techniques: the synthetic method, by means of phase equilibria, and the analytical methods requiring sampling and analysis.

1) The synthetic method is based on the visualization of the phase changes of solid-fluid or liquid-fluid binary mixtures in a thermostat-controlled high-pressure cell provided with a window (generally made of sapphire or quartz) whose volume can be varied through the displacement of a piston moving in a chamber. The cell is charged with a known quantity of solid or liquid compound. After several purges with gas ($CO_2$, methane) intended to draw the entrapped air away, a known quantity of gas is thereafter introduced into the cell. The phase changes of the mixture can then be observed by means of a camera placed against the window.

At a given temperature, the supercritical solid-fluid mixture contained in the cell is slowly compressed until the solid is solubilized by the fluid, a single phase being then present in the cell. The pressure is then slowly decreased until two phases appear. The mixture is alternately compressed and decompressed several times so that the pressure range for which a phase change is observed is as small as possible. Solubility in this pressure range is readily determined because the quantities of solid and of gas introduced in the cell are known with precision.

The synthetic method both presents advantages and drawbacks insofar as phase transitions are detected visually, the solubilities of the liquids and of the solids are obtained without sampling, the quantities of compound and of supercritical fluid used are small, and the devices used to implement the method are sophisticated and therefore expensive. An example of application of the synthetic method is described for example in:

McHugh M. et al: "Solid Solubilities of Naphtalene and Biphenyl in Supercritical Carbon Dioxide", J. Chem. Eng. Data, 1980, 25, 326–329.

2) Analytical methods are more commonly used to study solubility in supercritical fluids. The implementation devices can be used either to extract one or more solid compounds from a matrix, or to study the solubility of a solid compound in the supercritical fluid. In this case, the cell contains only the compound whose solubility is to be measured.

Implementation devices generally comprise in combination a solvent tank, a pump, an extraction cell, a recovery system and an analysis system. Their design, selection of the recovery system and of the analysis method differ according to the aim and to the solutes studied.

The main three analytical methods known for solubilization by supercritical fluids are the static method, the dynamic method and the semi-dynamic method halfway between the previous two methods.

2.1) The static method consists in bringing the compound into contact with a given volume of fluid. The supercritical fluid is introduced, then maintained in the extraction cell and mixed by stirring with the compound to be solubilized. The temperature is kept constant by a thermostat-controlled bath or a furnace. Prolonged contact between the fluid and the compound guarantees good equilibrium and therefore solubilization conditions. The quantity of supercritical fluid required is limited but the solubilization time required is longer and generally ranges from one to three hours. An example of use of the static method is described for example in:

Hollar W. P. et al: "Solubility of Naphtalene in Mixtures of Carbon Dioxide and Ethane", J. Chem. Eng. Data, 1990, 35, 271–275.

2.2) The dynamic method is most often used to measure the solubility in a supercritical fluid that is for example brought continuously in contact with the compound to be solubilized. The implementation device can be an open-circuit device, the pure supercritical fluid circulating through the compound to be solubilized. The flow rate of the supercritical fluid imposes the velocity of flow of the fluid through the compound, and therefore the contact time. The geometry of the solubilization cell and the characteristics of the solid compound (grain size) influence the search for equilibrium conditions. An example of implementation of an open-circuit device is described for example in:

Van Leer et al: "Solubilities of Phenol and Chlorinated Phenols in Supercritical Carbon Dioxide", J. Chem. Eng. Data, 1980, 25, 257.

In the dynamic mode, the solubilization time is shorter than in the static mode but the quantity of fluid used is greater.

2.3) In the semi-dynamic method, the previous two operating methods can be combined by prolonging, according to a dynamic mode, a short static period performed at the solubilization start when equalizing the pressures and the flow rate. Combination of these two modes allows improvement of the supercritical solid-fluid equilibrium and therefore to obtain quite readily solubility equilibrium, and it requires shorter solubilization times than the static mode. Such a semi-dynamic method is for example described in:

Yau J. S. et al: "Solubilities of Heavy n-Paraffins in Subcritical and Supercritical Carbon Dioxide", J. Chem. Eng. Data, 1993, 38, 171–174.

Analytical methods afford certain advantages in relation to synthetic methods. The cost of the equipment used is moderate. The experimental device can also be used for extraction. Sampling in the supercritical state prevents analysis errors due to precipitation in the relief valve.

3) Extract Recovery

After the solubilization process, a sampling has to be achieved in order to determine the solute concentration and to measure the volume of solvent gas. Sampling can be performed in the supercritical state or by expansion. According to the configuration, the sampling and analysis stages can be coupled, analysis being then performed on-line or off-line. The volumes sampled are very different according to the coupling type and to the analysis method.

In the supercritical state sampling mode, the supercritical fluids being gaseous at atmospheric pressure, the compound can be precipitated by simple expansion. The flow rate of the supercritical fluid and the expansion method influence the recovery percentage. Too high a flow rate can lead to losses upon expansion, especially for volatile solutes. The great majority of the devices are equipped with a HPLC type sampling valve for example which imposes the flow rate of the fluid, and therefore the pressure in the cell. This valve is heated in order to prevent precipitation of the solutes that might modify the flow rate upon expansion. Several collection modes can be envisaged. The compound can be recovered by cryogenic trapping in a cooled empty tube in order to increase the trapping efficiency and to prevent carry-over of the volatile compounds. The higher the flow of gas, the lower the required temperature. The recovery ratio is improved by adding for example an adsorbent in the tube or by using a cooled chromatographic column. The compound can also be collected by bubble-type recovery within the scope of an off-line analysis, or on an adsorbent after expansion. The extracts precipitate and are trapped on a stationary phase. This type of recovery has a better reproducibility than bubbling; the flow rates used can be higher, hence a greater analysis speed.

4) Analysis a) Analysis can be performed off-line for solubility studies since the sample is to be weighed, and also on-line with quantitative transfer of all of the compound sampled, which prevents pollution and guarantees high sensitivity, hence high accuracy.

Supercritical sampling can be directly coupled with various gas, liquid or supercritical chromatographic techniques and common detection methods can be used. The most delicate stage during coupling is the recovery of the solute prior to analysis and therefore the separation of the solute and of the solvent. Various techniques of coupling with gas, liquid or supercritical phase chromatography are described for example in:

Hawthorne et al: Directly Coupled Supercritical Fluid Extraction-gas Chromatographic Analysis of Polycyclic Aromatic Hydrocarbons and Polychlorinated Biphenyls from Environmental Solids—Journal of Chromatography, 1987, 403, 63–76;

Unger K. K. et al "On-Line High-Pressure Extraction-High-Performance Liquid Chromatography—Journal of Chromatography, 1983, 282, 519–526, or Jackson W. P. et al: Supercritical Fluid Injection of High-Molecular-weight Polycyclic Aromatic Compounds in Capillary Supercritical Fluid Chromatography, in J. HRC & CC, 1986, 9, 213–217.

SUMMARY OF THE INVENTION

A system according to the invention measures the solubility of solid compounds in supercritical fluids and notably in carbon dioxide or methane. It comprises a fluid delivery device delivering fluid in a supercritical state at a constant pressure, a saturation cell wherein the fluid saturates the compound to be dissolved and a saturated fluid reception device is connected to the saturation cell by means of a multi-way valve.

The fluid delivery device comprises a pump including a pressure regulator (which may be a concentration gradient type pump for example) associated with complementary pressure and a temperature regulator.

According to an embodiment, these complementary pressure and temperature regulators comprise a filter, a device which establishes a leak rate and a gas surge capacity, and a pump associated with a constant-temperature bath.

According to another embodiment, a saturation cell is provided with a strainer of controlled porosity.

According to another embodiment, a fluid flow control comprises a constant-pressure chamber connected to the saturation cell by means of the multi-way valve.

The constant-pressure chamber comprises for example a volume of mercury and mercury expansion device.

According to another embodiment, the saturation cell, the constant-pressure chamber and the multi-way valve are placed in a thermostatically-controlled enclosure.

The system preferably comprises a device suited for sampling and for bringing the sample into solution, coupled by a multi-way valve to an analysis device which includes a chromatographic column and a detector such as a spectrophotometer operating in the ultraviolet range.

The system preferably comprises a device which generates a pressure drop in order to control the pressure in an analysis device.

The saturation cell comprises for example an elongate chamber arranged vertically and circuits communicating the delivery device with the upper part of the chamber.

The analysis devices used are for example a liquid phase chromatograph or a spectrophotometer operating in the ultraviolet.

BRIEF DESCRIPTION OF THE DRAWINGS

Other features and advantages of the device according to the invention will be clear from reading the description hereafter of embodiments given by way of non limitative examples, with reference to the accompanying drawings wherein:

FIG. 4 diagrammatically shows the sampling and sample dissolving loop, as well as the analysis device, and FIG. 5 shows examples of variation curves of the solvent power of the fluid as a function of the pressure.

DESCRIPTION OF THE PREFERRED EMBODIMENTS OF THE INVENTION

I) System

The system according to the invention measures the solubility of various solid organic compounds in a supercritical fluid such as carbon dioxide, methane, etc, and permits study of the equilibrium between the solid phase and the supercritical phase in a pressure range between 7 MPa and 150 MPa for example and at temperatures ranging between 20 and 200° C. for example. The system combining a supercritical extraction and high-performance liquid chromatography coupling allows the performing of dynamic solubilization with on-line or off-line analysis of the sample.

Figure 1:
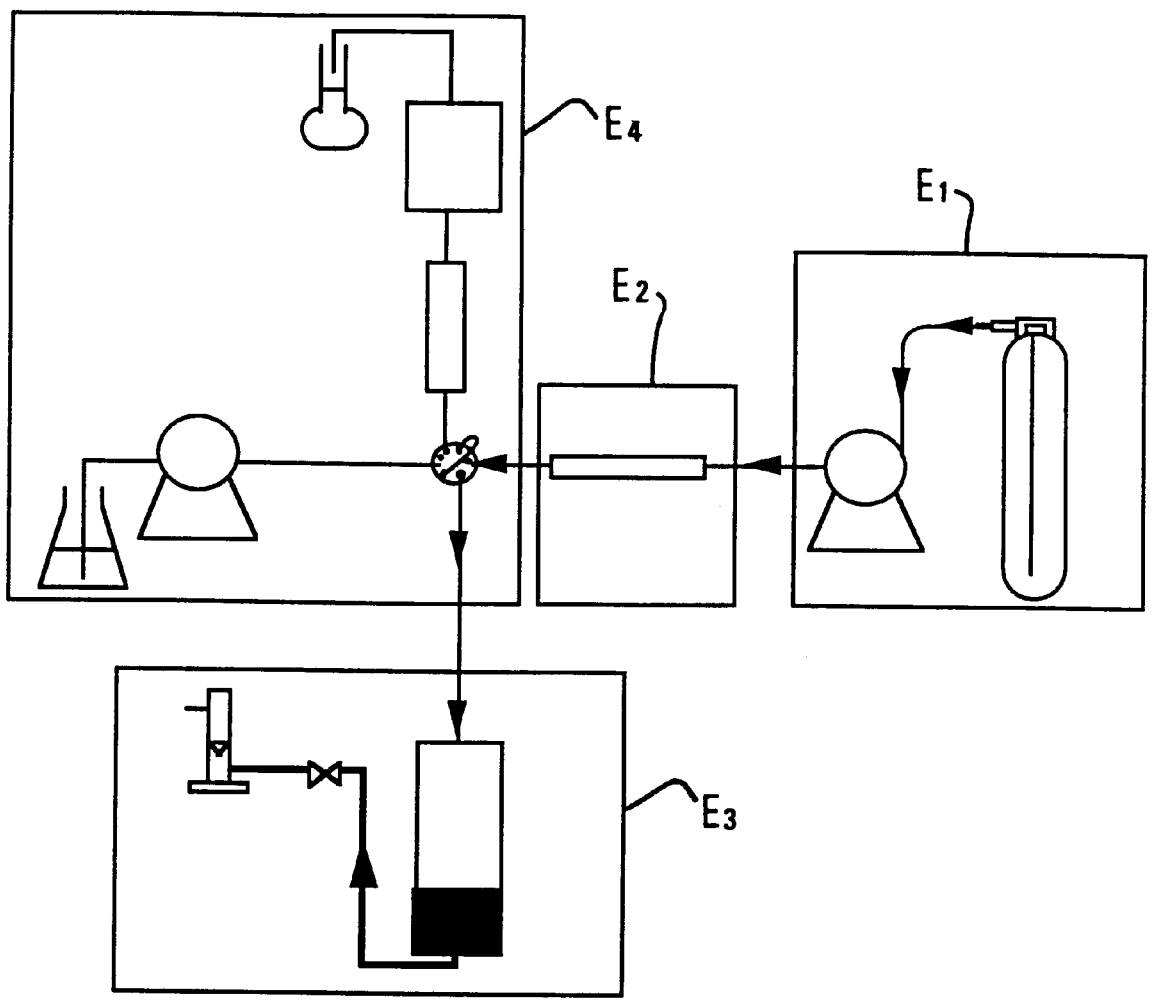
FIG. 1 shows the system in the form of functional blocks.

The system comprises (FIG. 1) four functional units E1, E2, E3, E4. Unit E1 delivers fluid under pressure ($CO_2$ for example), unit E2 comprises a sampling cell containing the compound to be solubilized, wherein the pressurized gas from unit E1 saturates the compound on contact therewith, unit E3 samples and brings the sample into solution, and unit E4 receives the saturated fluid and analyzes it.

In the functional units E1 to E4, particular attention has been devoted to the pumping and leakage system, adjustment of the fluid and leak system, adjustment of the fluid flow rate, the saturation cell, and analysis of the sample in order to keep a perfect pressure stability. In fact, as shown in FIG. 5, the quality of the measurements and notably the solvent power of the fluid is directly linked with the stability of the pressure, notably in the ascending part of the solubility isotherm.

Figure 2:
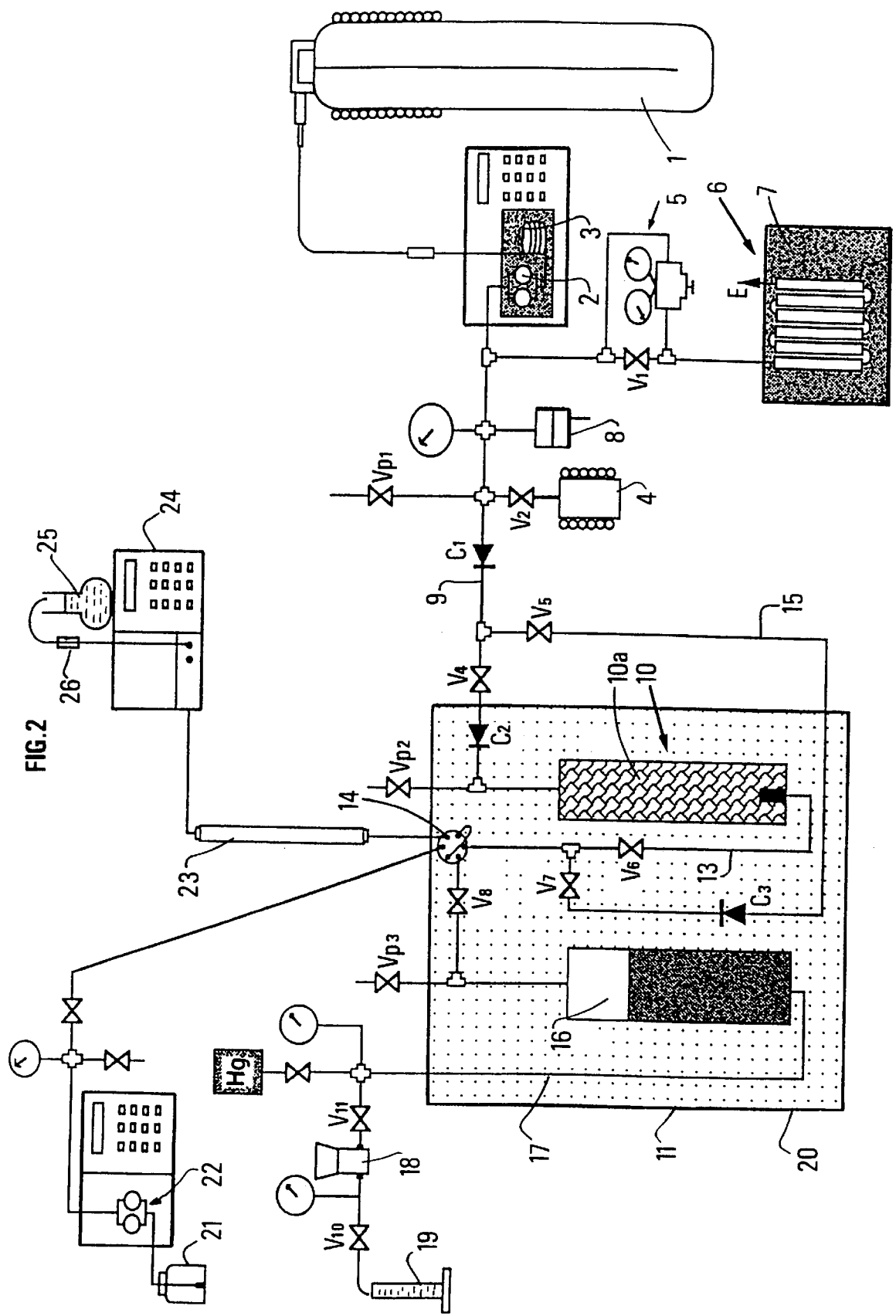
FIG. 2 diagrammaticallly shows the layout of the system.

1) Unit E1 comprises (FIG. 2) a dip-tube bottle 1 containing fluid under pressure, associated with an extraction pump 2 suited for high-pressure liquid chromatography (HPLC) with an incorporated pressure regulation that is quick enough to prevent great pressure variations.

A pump provided with a concentration gradient device allowing a co-solvent to be added to the solvent is preferably used, both being selected for selective extraction of a substance having a high degree of purity from a mixture.

A filter 3 is interposed between bottle 1 and pump 2. The fluid flows through filter 3, then it is cooled down to about 0° C. by circulation in an icy water bath. The heads of pump 2 are also immersed in this bath in order to prevent cavitation.

In order to ensure correct regulation and fast stabilization of the pressure, the assembly comprises an autoclave type surge capacity 4 accessible through a valve V2 and a regulated fluid leakage circuit comprising a by-pass expansion valve 5 on a circuit portion provided with a valve V1 and a pressure drop 6 consisting for example of several chromatography columns connected in series in a thermostatically-controlled bath 7 at 40° C. The leak rate can range between 10 and 100 $cm^3$/min (fluid flow rate measured under ambient conditions). A manometer 8 measures the pressure with an accuracy of ±3 Pa. It is equipped with a limiter that stops the feeding of pump 2 when the pressure reaches a predetermined limit. Manometer 8 is connected to a drain valve Vp. Unit E1 communicates with unit E2 through a line 9 comprising a non-return valve C1 in order to protect pressure detector 7 from a possible backflow of the saturated fluid. Long and delicate detector dismantling, cleaning and calibration operations are thus avoided. To decrease pressure drop, a ball check valve is preferably used, which introduces a lower pressure drop than spring check valves.

2) Unit E2 comprises (FIG. 2) a saturation cell 10 placed in a temperature regulated bath 11. A first end of cell 10 is connected to line 9 by a valve V4 and a ball check valve C2, and it communicates with a drain valve Vp2. The carbon dioxide under pressure circulates continuously through cell 10 and saturates with compound to be dissolved. The quantity of solubilized compound depends on the pressure and temperature conditions.

Figure 3:
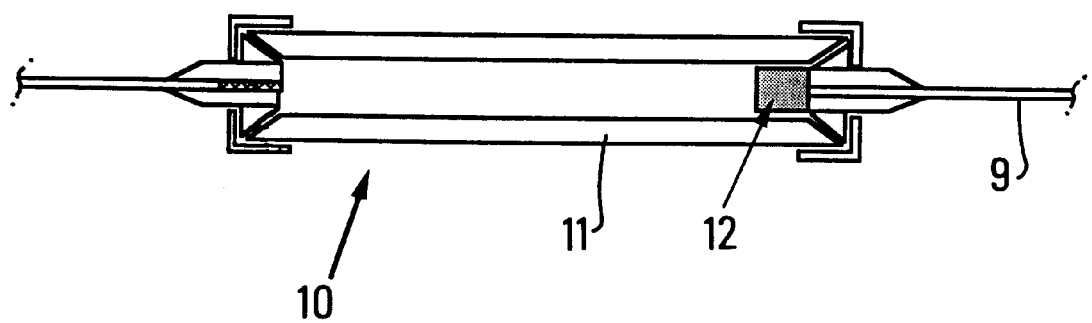
FIG. 3 diagrammatically shows the sampling cell.

Cell 10 comprises for example (FIG. 3) a stainless steel tube 11 connected to circuit 9 by conventional double-ring connectors. The crushed pure compound whose solubility is to be studied is directly charged into cell 10. A thermocouple (not shown) of copper-constantan type for example is placed against the wall of the cell and measures the equilibrium temperature. In order to prevent mechanical carry-over of the solid, the compound-saturated supercritical fluid leaves the cell through a strainer 12 situated at the bottom of the cell, whose porosity is for example 10 $\mu$m, which prevents mechanical carry-over of the compound.

3) Unit E3 intended for reception of the saturated supercritical fluid communicates through a line 13 (FIG. 2) with another end of sampling cell 10 by means of a six-way HPLC type valve 14 downstream from a valve V6. A circuit branch 15 bearing a valve V5 in series with a ball check valve C3 and a valve V7 connects circuit 9 to line 13 downstream from valve V6.

Six-way valve 14 is connected to the upper part of an autoclave 16 filled with mercury and accessible through a valve V8. The mercury acts as a piston which the fluid coming from cell 10 pushes away as it flows in. Expansion of the mercury is performed at the base of autoclave 16, through a line 17 provided with a stainless steel expansion valve 18 communicating with autoclave 16 by means of a valve V11. The leak rate of mercury can possibly be adjusted by a metering type valve V10 placed on a line connecting expansion valve 18 to a flowmeter 19. A drain valve Vp3 is connected to the upper part of the autoclave.

This layout contributes towards pressure stability, thus preventing precipitations of the compound that saturates the supercritical fluid favored by the presence of heptane in the circuit of this fluid beyond six-way injection valve 14. In fact, after sampling, the volume of the loop is filled with liquid solvent (heptane). When a second fluid sampling is performed, the solvent flows through the supercritical fluid circuit when the injection valve is back in the "loading" position. The nature and viscosity difference between the two phases leads to a precipitation.

Autoclave 16, saturation cell 10 and valve 14 are preferably placed in the same thermostatically-controlled bath 20 so that the saturated fluid remains at constant temperature and pressure.

4) Unit E4 (FIGS. 2, 4) communicates with unit E3 through HPLC valve 14. It comprises a flask 21 containing an organic solvent such as heptane for example, forming the eluent of a conventional high-pressure liquid chromatography system, and a programmable piston pump 22 for injecting solvent into a chromatographic column 23 through six-way valve 14. The outlet of this column 23 is connected to a detection device 24 such as a spectrophotometer operating in the ultraviolet.

Valve 14 allows sampling of known volumes of saturated supercritical mixture (20 to 284 or 551 $\mu$l for example). The compound dissolved in the supercritical fluid is brought into solution in the organic solvent taken from bottle 21. Expansion of the supercritical fluid and solubilization of the solute occur in chromatographic column 23. Unit E4 allows recovery of the sample to be controlled or an on-line analysis to be performed.

When valve 14 is in "loading" position, loop E4 is swept by the supercritical fluid coming from saturation cell 10. When this valve is in "injection" position, the fluid contained in the loop is driven by the eluent towards chromatographic column 20.

When valve 14 is shifted to the "injection" position, the supercritical fluid expands in column 23 because the outlet of the chromatographic system is at atmospheric pressure. Since chromatographic column 23 forms a pressure drop, the $CO_2$ can expand progressively. The solute dissolves in the solvent used (heptane for example) and the solution is collected in a 5, 10 or 25-ml volumetric flask 25 for example.

Analysis device 24 may be an isocratic chromatograph of a well-known type, associated with a holochrome series UV spectrophotometer of variable wavelength for detection, and with an integrator. The technique used is partition chromatography. The stationary phase is a 10-cm long and 4.6-mm internal diameter silica column for example. The mobile phase is the heptane that also forms the solvent of the extract.

To perform absorbance measurements, it is possible to use a double-beam spectrophotometer of a well-known type capable of scanning wavelengths from 200 to 800 nm. A deuterium lamp with an inlet slot width of 1 nm is for example used as the UV radiation source.

The HPLC chromatographic system is preferably used only to bring the extract into solution in a conventional solvent. After injection of the extract, the eluent is recovered quantitatively in a volumetric flask of variable volume (5, 10 or 25 ml) thus allowing high dilution. This operating method is simple, fast and well suited to the compounds studied.

II) Implementation

After crushing of the various constituents in a mortar so as to have a homogeneous grain size, the solid mixture is packed as it fills column 10.

In order to ensure correct pressure build-up and to prevent clogging when the equipment is set into operation, the following operating protocol is preferably followed:

a) Pump Priming

Supercritical fluid bottle 1 is opened (FIG. 2) and pump 2 is set into operation after display of a set pressure value. At this stage, all the valves are closed except for V1 and V2. Opening of an air pipe E causes a high leak rate, which allows to purge the circuit and to prime the pump properly, the presence of air preventing any pressure increase. After priming, valve V1 is closed.

b) Introduction of the Supercritical Fluid into the Saturation Cell

When the desired pressure is reached and stable, the saturation cell is placed under pressure by opening valve V4. This valve is thereafter closed as soon as the pressure has reached its set value again.

c) Circulation of the Supercritical Fluid at a Determined Flow Rate

Valves V5, V7 and V8 are respectively opened to place autoclave 16 containing the mercury under pressure while bypassing saturation cell 10. When the pressure reaches the desired value, valve V11 and metering valve V10 are opened so as to have a flow rate of mercury of about 0.1 $cm^3$ $min^{-1}$, the latter being measured with a test tube and a chronometer. When the leak rate of mercury is stable at the desired value, V4 is opened and V5 and V7 are simultaneously closed, then V6 is opened. This operation causes circulation of the supercritical fluid in saturation cell 10.

d) Sampling

The saturated supercritical fluid is allowed to circulate for a few minutes in the assembly to check the pressure stability. In order that the fluid circulates in the sampling loop, HPLC injection valve 14 is switched to the "loading" position.

The loading time of the loop depends on the volume thereof. It corresponds to the passage of a quantity of fluid equal to about ten times the volume thereof. For 20, 284 and 551-$\mu$l loops, fluid volumes of respectively 2, 2.5 and 5 ml for example are allowed to circulate. The volume of fluid circulating through the loop is directly given by the volume of mercury recovered in test tube 19.

HPLC valve 14 is thereafter switched into the "injection" position; the fluid contained in the loop is driven along and solubilized by the eluent phase of the chromatographic system. The solution is then recovered in volumetric flask 25.

e) Stopping

To stop the device without causing clogging, the three parts of the assembly have to be isolated in reverse order in relation to that followed for placing them under pressure: pump 2, saturation cell 10 and autoclave 16 which contains the mercury.

Circulation of the fluid is stopped by closing metering valve V10. Autoclave 16 is then isolated from saturation cell 10 by closing valves V6 and V8. Finally, the saturation cell is isolated from pump 2 by closing valve V4.

The saturated fluid contained in autoclave 16 is expanded by opening drain valve Vp3; when the pressure is equal to the atmospheric pressure, drain valve Vp3 is closed. Autoclave 16 is thereafter rinsed with pure $CO_2$ in order to remove the precipitated solute by opening valves V5, V7 and V8.

When the pressure reaches about 25 MPa, V8 is closed and drain valve Vp3 is opened. This operation is repeated three or four times, then valves V8, V7, V5 are closed.

To expand saturation cell 10, drain valve Vp2 is opened slowly so as to prevent clogging at the level of this valve.

After stopping the pump and closing supercritical fluid bottle 1, the circuit is expanded by means of drain valve Vp3. When the pressure is about 5 MPa, drain valve Vp3 is closed and leakage valve V1 is opened. The residual pressure slowly expands through the leak.

On-Line Analysis

To prevent any expansion of the supercritical fluid in the liquid circuit, which disturbs UV detector 22 and prevents quantitative analysis, the flow rate of the mobile phase and the pressure drop caused by chromatographic column 20 are adjusted so as to have the same pressure in the supercritical part (E2, E3) of the system and in the analysis system (E4). This adjustment is achieved by interposing for example a device 26 creating a pressure drop (FIG. 4) between flask 25 and detector 24 to maintain the latter under pressure.

Off-Line Analysis

For off-line analysis, the system is used only to bring the extract into solution in a conventional solvent. After injection of the extract, the eluent is recovered quantitatively in a volumetric flask of variable volume (5, 10 or 25 ml) thus allowing high dilution.

We claim:

1. A system for measuring solubility of solid compounds in a supercritical fluid, comprising a fluid delivery device delivering fluid in a supercritical state under constant pressure, a saturation cell in which the fluid saturates the solid compound to be dissolved and a saturated fluid reception device connected to the saturation cell by a valve; and wherein the fluid delivery device comprises a pump which pumps the supercritical fluid and an associated pressure regulator which regulates pressure of the supercritical fluid pumped by the pump and temperature regulator which regulates temperature of the pumped fluid.

2. A system as claimed in claim 1, wherein:

the fluid delivery device comprises a filter, a device which establishes a leak rate and a gas surge capacity and the pump is associated with a constant-temperature bath.

3. A system as claimed in claim 2, wherein:

the saturation cell includes a strainer of controlled porosity.

4. A system as claimed in claim 3, wherein:

the pump is a concentration gradient type which selectively injects two fluids.

5. A system as claimed in claim 2, wherein:

the pump is a concentration gradient type which selectively injects two fluids.

6. A system as claimed in claim 1, wherein:

the saturation cell includes a strainer of controlled porosity.

7. A system as claimed in claim 6, wherein:

the pump is a concentration gradient type which selectively injects two fluids.

8. A system as claimed in claim 1, further comprising:

a supercritical fluid flow adjustor including a constant-pressure chamber connected with the saturation cell by the valve.

9. A system as claimed in claim 8, wherein the constant-pressure chamber comprises a volume of mercury and a mercury expansion collection device.

10. A system as claimed in claim 9, wherein:

the saturation cell comprises an elongate chamber arranged vertically and circuits for coupling the delivery device to an upper part of the constant pressure chamber.

11. A system as claimed in claim 9, wherein:

the saturation cell, constant-pressure chamber and the valve are placed in a thermostatically controlled enclosure.

12. A system as claimed in claim 11, wherein:

the saturation cell comprises an elongate chamber arranged vertically and circuits for coupling the delivery device to an upper part of the constant pressure chamber.

13. A system as claimed in claim 8 wherein:

the saturation cell comprises an elongate chamber arranged vertically and circuits for coupling the delivery device to an upper part of the constant pressure chamber.

14. A system as claimed in claim 1, further comprising:

a utilization device which is coupled to the reception device, and which samples a sample, brings the sample into solution and analyzes the sample.

15. A system as claimed in claim 14, wherein:

the utilization device comprises a device which generates a pressure drop to control pressure in the analysis device.

16. A system as claimed in claim 15, wherein:

the analysis device comprises a liquid phase chromatograph.

17. A system as claimed in claim 15, wherein:

the analysis device comprises a spectrophotometer operating in an ultraviolet range.

18. A system as claimed in claim 15, wherein:

the analysis device comprises a spectrophotometer operating in an ultraviolet range.

19. A system as claimed in claim 14, wherein:

the analysis device comprises a liquid phase chromatograph.

20. A system as claimed in claim 1, wherein:

the pump is a concentration gradient type which selectively injects two fluids.

21. A system as claimed in claim 1 wherein:

the valve is a multi-way valve.

* * * * *